United States Patent [19]

Eykmann et al.

[11] Patent Number: 5,246,105
[45] Date of Patent: Sep. 21, 1993

[54] MODULAR CONTAINER FOR DENTAL PHOTOCURING MATERIALS

[75] Inventors: Rudolf Eykmann, Wehrheim/Ts.; Joachim Fritze, Friedrichsdorf; Birgit Uhrig, Usingen, all of Fed. Rep. of Germany

[73] Assignee: Heraeus Kulzer GmbH, Hanau, Fed. Rep. of Germany

[21] Appl. No.: 753,705

[22] Filed: Sep. 3, 1991

[30] Foreign Application Priority Data

Sep. 4, 1990 [DE] Fed. Rep. of Germany ... 9012753[U]

[51] Int. Cl.$^5$ .......................................... B65D 25/02
[52] U.S. Cl. ................. 206/63.5; 220/4.27; 220/345; 312/107
[58] Field of Search ......................... 206/368–370, 206/372–373, 459, 63.5, 459.5; 220/4.01, 4.26–4.28, 345; 312/107, 209, 311, 198, 201, 263, 264, 293, 309

[56] References Cited

U.S. PATENT DOCUMENTS

| 1,253,546 | 1/1918 | Vanderveld | 312/107 |
| 1,619,761 | 3/1927 | Rand | 312/107 |
| 1,857,640 | 5/1932 | Johnson | 312/107 |
| 2,004,900 | 6/1935 | Nock | 312/107 |
| 3,133,771 | 5/1964 | Dorman | 312/107 |
| 3,409,162 | 11/1968 | Mahlich et al. | 220/4.28 |
| 3,529,878 | 9/1970 | Blowers | 312/107 |
| 3,606,506 | 9/1971 | Ungaro | 312/107 |
| 3,729,242 | 4/1973 | Barney | 312/107 |
| 3,758,181 | 9/1973 | Bolyos | 312/107 |

FOREIGN PATENT DOCUMENTS

| 0069897 | 9/1915 | Austria | 312/107 |
| 956836 | 1/1957 | Fed. Rep. of Germany . | |
| 2141163 | 2/1972 | Fed. Rep. of Germany . | |
| 2449895 | 4/1976 | Fed. Rep. of Germany . | |
| 3142675 | 5/1983 | Fed. Rep. of Germany . | |
| 8607133 | 6/1986 | Fed. Rep. of Germany . | |
| 8708987 | 10/1987 | Fed. Rep. of Germany . | |
| 8802420 | 6/1988 | Fed. Rep. of Germany . | |
| 3720409 | 7/1988 | Fed. Rep. of Germany . | |
| 0055907 | 11/1935 | Norway | 312/107 |
| 0254759 | 5/1948 | Switzerland | 312/107 |

OTHER PUBLICATIONS

Kulzer & Co. GmbH brochure 5288/ D 218 SK, entitled Dentacolor Lichthartendes K+B Composite auf Micorill-Basis, publ. 1988, pert. pp. 5–6.

Primary Examiner—Jimmy G. Foster
Attorney, Agent, or Firm—Frishauf, Holtz, Goodman & Woodward

[57] ABSTRACT

A modular container for dental materials has an upper section (1) with a hinged top (13) and a lower section (2) composed of at least two superposed modules (3), each with two drawers (4). All sections feature interchangeable side panels (5) connected by aluminum sheet (6; 6') or the like, which is bent to form both a rear wall (8; 8') and a base element (7) or a cover element (20). The sheet metal is held between the side panel pair (5) by rails (32; 32'; 32") formed thereon. Similar rails (11; 11'; 11") formed on the inside of the front panels (25) engage around a laterally extending rim (22) at the front or back of each drawer; the drawers can be rotated front-to-back by attaching the front panel to the opposing edge. The upper section's cover is attached by hinges (12) which have rotational stops (14,15) for propping the cover in an open position. Hooks or barbs (26) atop each side panel (5) engage in slots or recesses (27) in the immediately superposed module or section, so that the modular unit stays together regardless of vibration. Rubber feet (28) under the bottom module damp vibration and provide glide races (29) for ribs (21) underneath drawers (4).

20 Claims, 4 Drawing Sheets

MODULAR CONTAINER FOR DENTAL PHOTOCURING MATERIALS

FIELD OF THE INVENTION

The present invention relates generally to a modular container for storage by dentist of materials for creating bridges, crowns and the like. More particularly, it relates to a container having a lower section and an upper section placed on top of the lower section, the lower section being composed of drawers and side panels, and the upper section having a hinged rotatable cover.

BACKGROUND

An earlier model of a container for the same purpose, previously sold by the assignee of the present invention, is described in brochure number 5288/D 218 SK, published in 1988, the English translation of whose title is "DENTACOLOR Light-hardening K+B Composite on Microfill Basis". This brochure illustrates a dental material assortment box, which has connectable drawer sleeves. These drawer sleeves are formed as compact elements consisting of a cover piece, side pieces and a rear piece. Multiple drawer sleeves are stacked above one another, with the lowest drawer sleeve sitting on a base plate. In each drawer sleeve, there is an integrally formed drawer, whose front panel is formed with a protruding hand grip. On top of the cover plate of the upper most drawer sleeve of this lower section, there is an upper section. This upper section consists of a drawer, as found in the drawer sleeves of the lower section, and of a cover, preferably transparent, which can be removed and inverted when not in use. The upper section is placed on top of the lower section This prior art structure is relatively costly to manufacture because special forms and tools, such as injection molds, are required and are complex. Another disadvantage is that this assortment box is relatively unstable, because the upper section is merely stacked on top of the lower section and the cover of the upper section is not attached, but merely fitted on by its lower peripheral edge.

THE INVENTION

Accordingly it is an object of the present invention to devise a container for storage of dental materials, which is economical to manufacture, uses a minimal number of different parts, yet offers both high variability or flexibility and a stable construction Briefly, this is accomplished by using a plurality of identical side panels which interengage with one another, by connecting the side panels with connecting pieces which define an integral rear part and base plate or cover plate, and by connecting the upper section to adhere its cover by a pair of hinges.

The use of identical side panels makes them readily interchangeable. Their substantially planar structure makes the molds and tools for their manufacture relatively simple to produce. The push-on connections between the side panels and the base or cover parts enable uncomplicated assembly of the upper section and of the models of the lower section. The fact that the front panels of the drawers are removable offers the possibility of also using the drawers outside of the assortment box.

The above-described structure permits arbitrarily great extension of the assortment box, since the individual elements are interchangeable and can be sequentially interengaged to any extent desired.

It is also advantageous that the plate-like connecting part has a right-angled rear portion, which forms the rear wall of the module or upper section This increases the stability of the module or upper section It is preferred that the plate-like connecting part of the upper section forms the base element of that upper section and that, from the base section, there extends a front panel up to about half the height of the upper section. Thus, the upper section forms a container in which, for example, dental materials or containers for receiving dental materials can be placed.

The embodiment of FIG. 4, in which the plate-like connecting part of the lower section defines a cover element, has the advantage that the drawers are covered, even when only a single module is used.

It is advantageous that the side panels have on their inward facing surfaces securing elements or rails, between which the edges of the plate-like connecting part can be clamped. This permits an uncomplicated assembly of the module or of the upper section.

In order to assure particularly high stability and resistance to any spilled dental materials, the plate-like connecting parts may comprise aluminum sheet.

It is desirable that the side panels have, on their inward facing surfaces, respective rails, which run substantially parallel to the upper and lower edges of the side panels and between which the drawers are slide. This permits exact guidance of the drawers and at easy handling.

In order to increase the stability of the individual drawers, even outside the assortment box, it is desirable that each drawer have on its under surface a rib or ridge running parallel to its corner edges.

For better handling of the drawers, it is advantageous that each drawer have a laterally extending rim or flange on its sides adjacent the front and rear sides of the assortment box and that the underside of this ridge or flange have a plurality of bumps or knobs. With the help of this rim, the drawer can be more easily drawn out of the assortment box. The fact that this laterally extending rim is provided on two opposing sides of the drawer makes it possible to slide the drawer into the assortment box, selectively, with either of these two sides first. This provides good accessibility to objects which might otherwise be in the rear most part of the drawer.

Preferably, a ridge or bead runs along the underside of the drawer near the edge and parallel to the laterally extending flange. With the help of this bead, the front panel can be better secured to the drawer For fastening of the drawer front panel on to the drawer, the drawer-adjacent face of the front panel preferably has two rails running parallel to the upper edge of the front panel, between which the laterally extending rim of the drawer is clamped. Further, the lower rail has a sequence of holes which correspond to and engage with the bumps or knobs on the drawer rim. A flange extending from the lower edge of the drawer front panel has on its upper surface a longitudinal groove into which the bead or ridge on the underside of the drawer engages. This assures a sufficiently stable connection between the drawer and its front panel, yet permits subsequent removal of the front panel if necessary.

In order to increase this stability of the assortment box when multiple modules are used, it is desirable that the upper edges of the side panels have connecting hooks or barb elements which engage in the lower edges of the side panels of the subsequent modules. This assures a fixed positioning of the superposed modules.

It is desirable that the lowermost side panels have on their undersurface recesses in which rubber elements are arranged which extend downward and laterally. The elasticity of these rubber elements tends to damp any vibration of the side pieces against one another and the rubber elements simultaneously serve as feet for the assortment box.

The lowest drawer of each module can have parallel ribs or ridges which engage in a longitudinal groove in the upper surface of the rubber elements. This further increases the stability of the assortment box and counteract any tendency for the side pieces of the lowest module to spread apart.

Advantageously, the cover of the upper section is rotatably connected at its rear corner with the upper section. This results in easy handling of the upper section and in good accessibility to the materials located in the upper section.

In order to stabilize the rotational movement of the cover of the upper section, the cover can be secured with hinges. In order to prevent a complete flip-over of the cover and resulting impact against the rear wall of the assortment box, it is desirable for the hinges to be equipped with a rotational stop.

A further possibility for fixing the position of the cover in the opened state is to provide stop elements on the gliding surfaces on the hinges.

The preferred form of the cover of the upper section is for the upper section's front panel to depend from the forward edge of the cover plate.

The front panels can be formed with gripping surfaces along their lower edge. This assures that easy handling of the drawers and of the upper section.

To assure easy handling of the assortment box, it is desirable that the drawer front panels and the cover front panel to have recesses extending from the upper corner to the lower corner. All recesses have the same width and are located at the same distance from the side corners of their respective parts. In these recesses one can secure signs, labels or descriptions of the content of the drawers or of the upper section.

Inside the assortment box, the facing surfaces of the side panels of the upper section can be equipped with camouflage panels secured to the rails of the side panels. This serves to hide the rails and to present flat surfaces in the interior of the upper section of the assortment box.

DRAWINGS

A preferred embodiment of the invention will be described with reference to the following drawings, of which, FIG. 1 is a perspective view of the modular container of the present invention;

DETAILED DESCRIPTION

The assortment container of the present invention has an upper section 1 and a lower section 2. Lower section 2 consists of two modules 3. Each module features two drawers 4.

Figure 5:
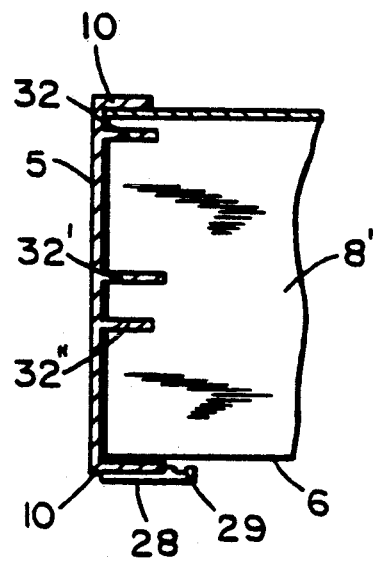
FIG. 5 is a sectional view, partially broken away, taken along a line I—I of FIG. 4.

The side panels 5 of the upper section and of modules 3 of lower section 2 are identical to each other and are symmetrical about a line perpendicular to their upper and lower corners. Thus, all the side panels are interchangeable and can be substituted for one another. Each two side panels 5 are coupled together by a planar connecting part 6, 6', preferably of aluminum sheet. As shown in FIG. 5, side panels 5 each have an inwardly directed circumferential edge 10 and three rails 32, 32', 32" which extend parallel to the upper and lower edges of side panels 5. Connecting part 6, 6' is clamped between rails 32, 32', 32".

Figure 2:
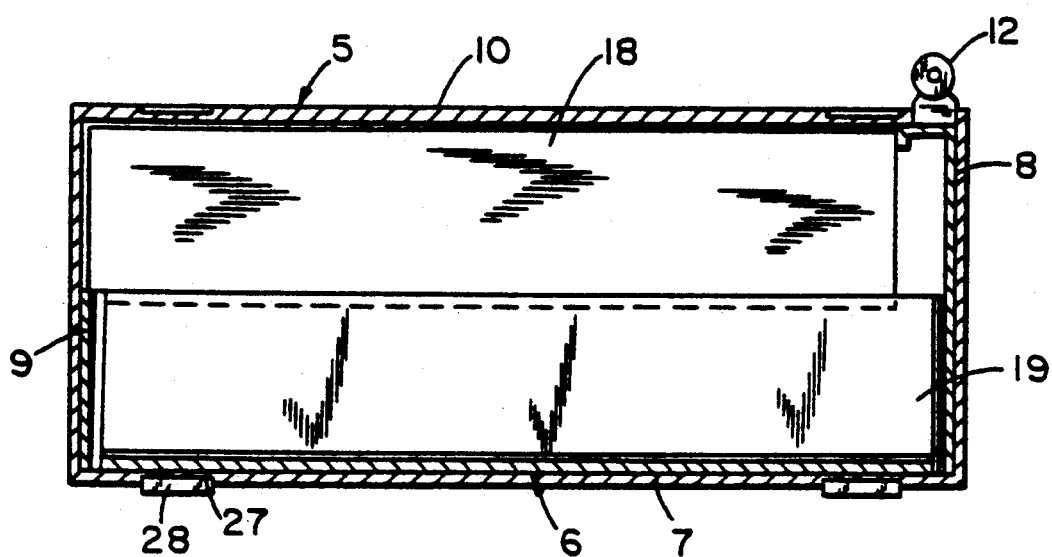
FIG. 2 is a sectional view of the upper section of the container of FIG. 1.

As best shown in FIG. 2, the upper section's connecting part 6 serves as the floor portion 7 of upper section 1. Part 6 has a right-angled rear portion 8 which forms the rear wall of upper section 1. At the front side of upper section 1, a front panel 9 is placed perpendicularly on floor portion 7. Front panel 9 extends upward about half the height of section 1. Rear portion 8's upper edge is bent over toward the interior of upper section 1 and, on the thus-created surface, two hinges 12 are mounted for fastening of a cover 13 of upper section 1.

Figures 8, 9:
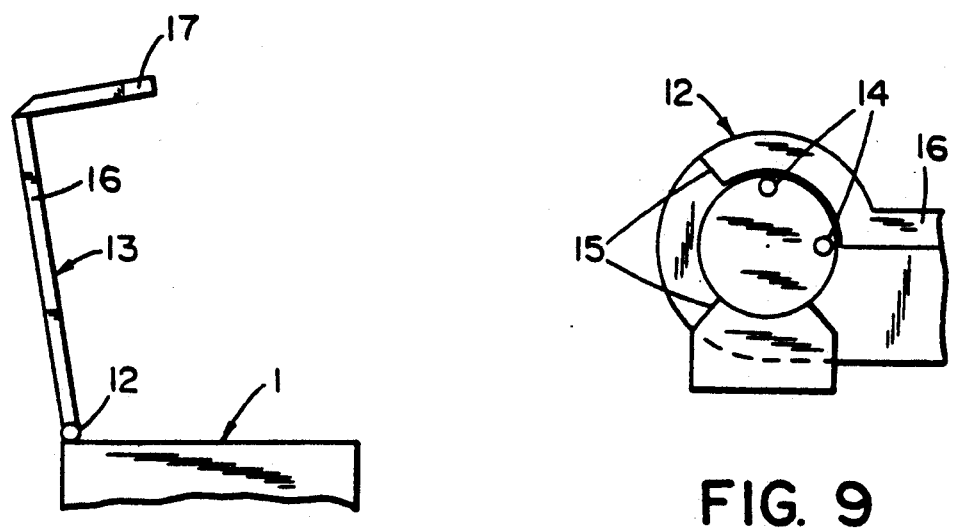
FIG. 8 is a side view of the cover of the upper section, rotated to a propped-open position.
FIG. 9 is an enlarged schematic view of the hinge of FIG. 8 in the close position, illustrating the stops used to prop the cover in an open position.

As shown in FIG. 9, hinges 12 have, on their gliding surfaces, stop or detent elements 14 which permit rotating cover 13 open to a position about 3° beyond the vertical or perpendicular (FIG. 8). If the stop elements should fail to prevent rotational overshoot by the cover, the rotating and stationary elements of hinges 12 each have a flat surface 15 (FIG. 9), and the two surfaces 15 impact one another, a few degrees after overshoot beyond the stop point, to keep cover 13 from falling over backwards.

Figure 3:
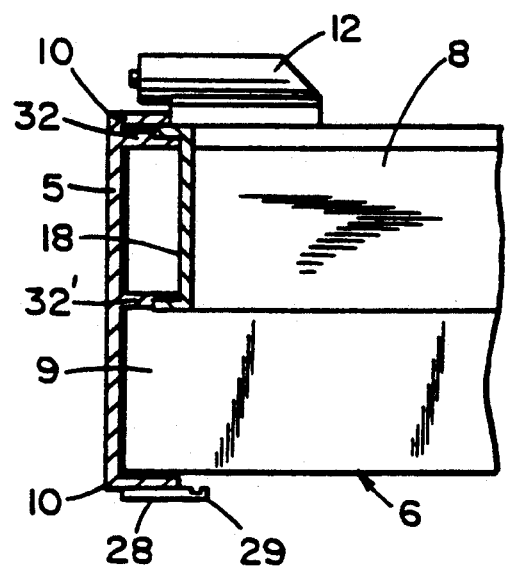
FIG. 3 is a front sectional view, partially broken away, of the container of FIG. 1.

As shown in FIG. 8, cover 13 consists of a flat cover plate 16 and a front portion 17 which depends from the front edge of cover plate 16. When cover 13 is closed, portion 17 closes off the front of upper section 1. In upper section 1, the rails 32, 32', 32" projecting from side panels 5 are perceived as disturbing, so they are preferably covered by camouflage elements 18 which are mounted on rails 32, 32', 32" of side panels 5, as shown in FIG. 3.

In upper section 1, one can place, for example, a receptacle 19 (not shown) for dental material.

Figure 4:
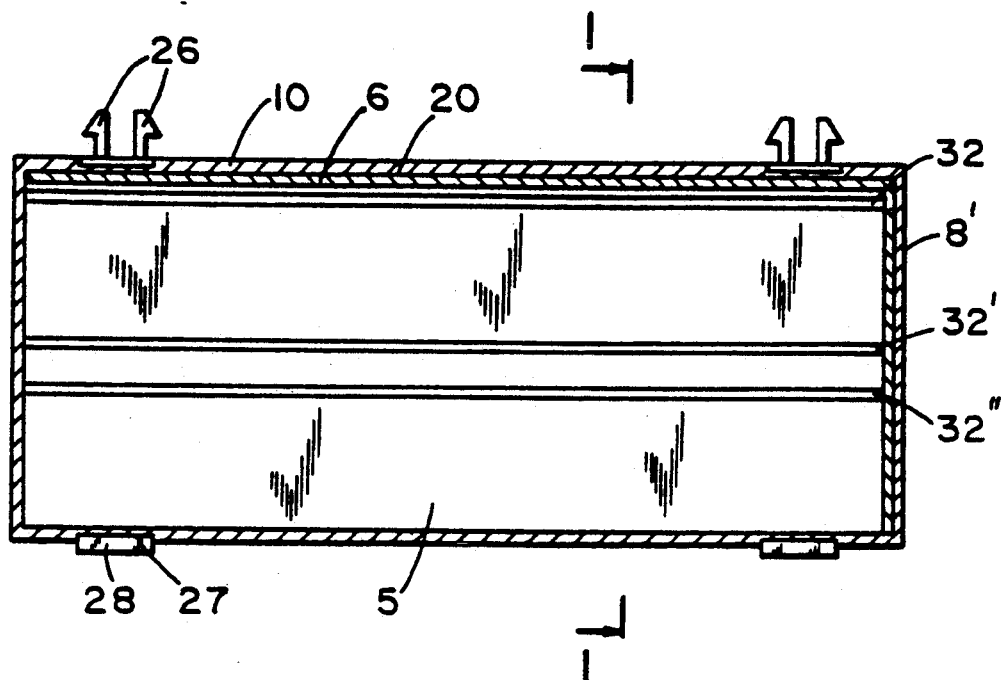
FIG. 4 is a side sectional view of one of the two lower section modules which engages under the upper section of FIG. 2.

Side panels 5 of modules 3 of lower section 2 are held together by connecting parts 6' in such a manner that, as shown in FIG. 4, these connecting parts 6 serve as cover elements 20 supporting a right-angled rear panel 8' which forms the rear wall of the respective module 3. As shown in the partially sectional FIG. 5, each connecting part 6', as in upper section 1, is clamped between the peripheral rim 10 of side panel 5 and rails 32, 32', 32" of side panel 5.

Figure 6:
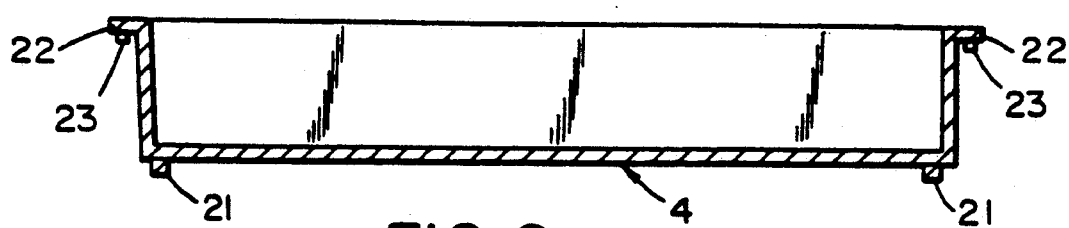
FIG. 6 is a sectional side view of a drawer.

Each side panel 5 engages two drawers 4, with the upper drawer 4 being guided between the two upper rails 32, 32' and the lower drawer 4 being guided between the lower rail 32" and the peripheral rim 10 of side panel 5. As shown in FIG. 6, each drawer is formed with a downwardly protruding ridge 21, running parallel to the drawer corner edges. This assures, for example, a steady stance of drawer 4 even when it is out of the assortment box.

Figure 7:
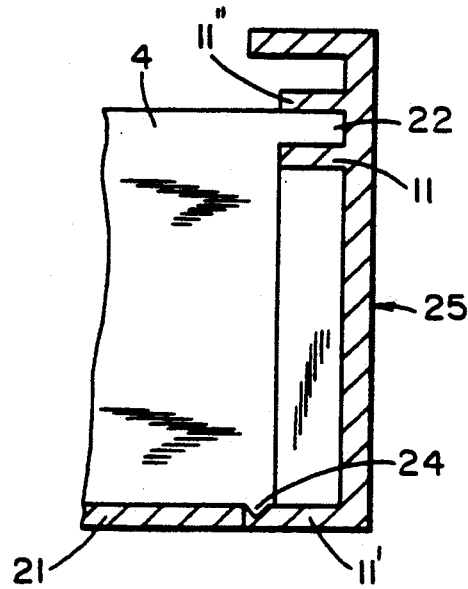
FIG. 7 is an enlarged sectional view showing the fastening of the front panel onto the drawer.

Each drawer 4 has, as shown in FIGS. 6-7, on its front- and rear-side adjacent corners, a laterally extending upper rim 22, on whose underside bumps or knobs 23 are formed. Further, on the underside of each drawer 4, along the corner edge parallel to the rim 22, there is a bulge or bead 24 between rim 22 and ridge 21. With the help of lateral rim 22 and bead 24, a drawer front element 25 is fastened on drawer 4. On the drawer-adjacent side of element 25, there are formed a pair of rails 11, between which are clamped the upper rim 22.

In the lower rail 11 are formed holes corresponding to the bumps or knobs 23 of drawer 4. Knobs 23 engage in and are detained in these holes, thereby snap-fitting front panel 25 onto drawer 4. Extending from the bottom edge of front panel 25, and running parallel to rails 11, 11" there is a flange 11', whose upper surface is formed with a longitudinal groove, running parallel to the plane of front panel 25. The bead or ridge 24 which protrudes from the front bottom edge of drawer 4, engages in this longitudinal groove, thereby stabilizing the lower end of front panel 25.

FIG. 4 illustrates a preferred way of stably connecting modules 3 of lower section 1 and upper section 1 together. Near the upper front corner and the rear corner of each side panel 5, a respective pair of hooks or barbs 26 protrude upward. These hooks have flat sides parallel to the outer surface of side panels 5. Each pair of hooks engages in a slot or recess 27 in the underside of side panel 5 of the adjacent module 3. The lowest module 3 of course receives no hooks from below, so its recesses 27 are filled by rubber feet 28, which protrude slightly below the undersurface of side panels 5 and extend slightly beyond the inner facing surfaces of side panels 5, as shown in FIG. 5. The upper surface of this projecting portion of rubber element 28 is formed with a longitudinal groove 29, running parallel to side panel 5, in which ridge 21 of the drawer above it rides.

Figure 1:
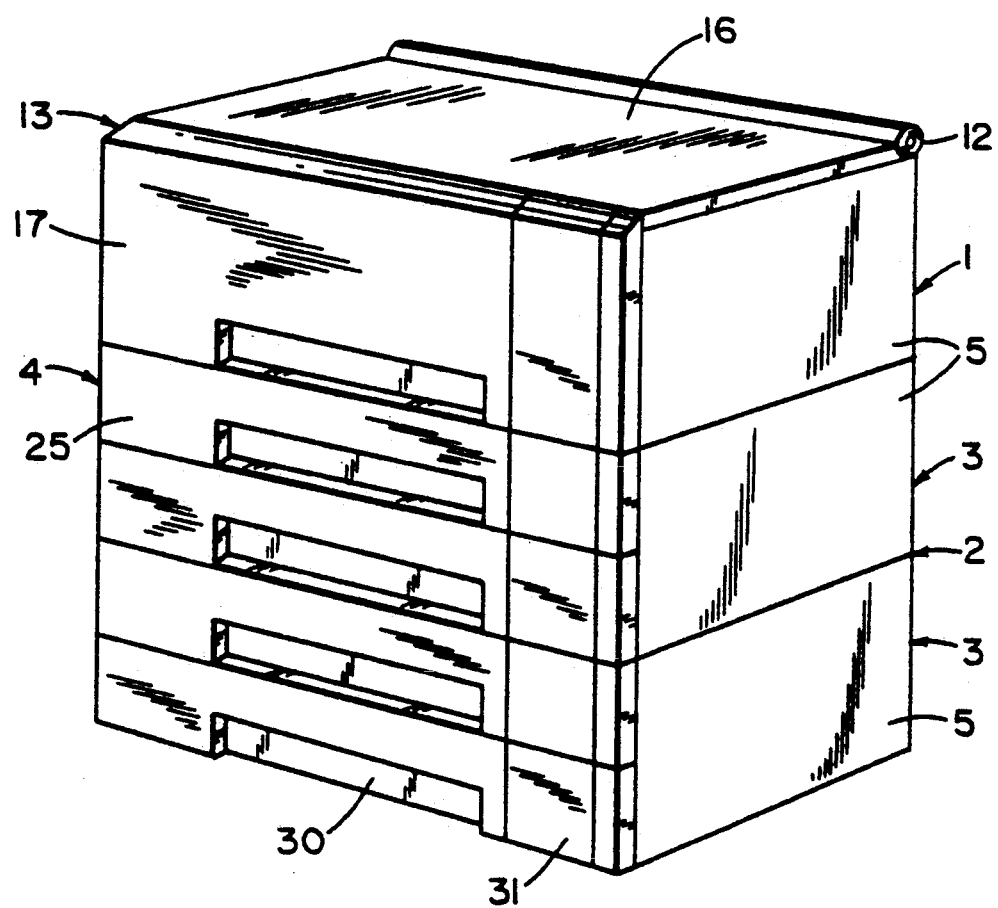

As shown in FIG. 1, the lower middle portion of each front panel 25 is formed with a hand grip recess 30. Between the gripping recess 30 and the outer side corners of each front panel 25, there are recesses 31, running from the upper corner to the lower corner, in which one can place labels or similar designations of the contents of the respective drawers or of upper section 1. These may be clamped, adhered or otherwise secured in any suitable and well-known manner.

We claim:

1. Modular container for storing dental materials, having
   a lower section (2);
   an upper section (1) which rests on said lower section;
   wherein said lower section has drawers (4);
   said upper section has side panels and a cover (13);
   said lower section includes a plurality of stacked modules (3) having side panels, each module containing two of said drawers (4);
   said side panels of said upper section and of said modules are formed similar to each other to make them interchangeable;
   said side panels of said modules include means (26,27) for releasably interengaging said side panels of respective ones of said stacked modules;
   two spaced-apart ones of said side panels of each module define a pair of said side panels, and each pair of said panels is interconnected by
   a respective connecting part (6) which engages said pair of side panels (5) and forms at least one of a base element (7) and a cover element (20);
   each drawer is releasably secured to
   a front panel (25); and
   said upper section (1) has a substantially planer cover plate (16) and a front panel (17) depending therefrom.

2. Modular container according to claim 1, wherein each connecting part (6; 6') includes
   a right-angled rear part (8) which forms a rear wall of a respective one of said modules (3).

3. Modular container according to claim 2, further comprising
   a connecting part (6; 6') of said upper section (1) serves as a base element (7) of the upper section, and a partial front panel (9) extends upward from said base element about half of a height dimension of said upper section (1).

4. Modular container according to claim 1, wherein each connecting part (6') in said lower section is a cover element (20) of one of said modules.

5. Modular container according to claim 1, wherein said side panels (5) are formed on their inner, facing surfaces with holding elements (10, 11), between which edges of said connecting parts (6; 6') can be clamped.

6. Modular container according to claim 1, wherein said connecting parts (6) are aluminum sheet material.

7. Modular container according to claim 1, wherein said side panels (5) of said modules are formed on their inner, facing surfaces with rails (32; 32'; 32") running parallel to upper and lower edges of said side panels (5), and along which said drawers (4) can be guided.

8. Modular container according to claim 1, wherein each drawer (4) has along its underside a ridge (21) extending parallel to edges of said drawer.

9. Modular container according to claim 8, wherein along an underside of each drawer, parallel to a laterally extending rim (22), there is a ridge or bead (24).

10. Modular container according to claim 9, wherein each drawer front panel (25) has a flange (11') extending from its lowermost edge, said flange being formed with a groove into which said ridge or bead (24) engages;
    each drawer front panel has a pair of rails (11; 11"), one of which is formed with holes which engage bumps or knobs (23) formed on said laterally extending rim of each drawer (4).

11. Modular container according to claim 1, wherein the container has a front said and a back side;
    each drawer (4) has along sides thereof, adjacent front and back sides of the container, laterally extending rims (22), whose undersurfaces are formed with bumps or knobs (23).

12. Modular container according to claim 1, wherein said means for releasably interengaging said side panels (5) comprise a slot-like recess (27) formed on an undersurface of each panel and
    a connecting element (26) formed on an upper surface of each panel which connecting element engages in the recesses of any superposed side panel (5).

13. Modular container according to claim 12, further comprising rubber elements (28) which engage in said recesses in a lowermost one of said modules, and extend downward below said side panels of said lowermost module.

14. Modular container according to claim 13, wherein said rubber elements are formed with respective grooves (29) and an underside of each of said drawers is formed with ridges (21) which ride in the grooves (29) formed in said rubber elements (28).

15. Modular container according to claim 1, wherein said cover (13) of said upper section (1) is rotatably connected at rear corners thereof to said upper section.

16. Modular container according to claim 1, wherein said cover (13) of said upper section (1) is connected to said upper section by hinges.

17. Modular container according to claim 16, wherein said hinges are equipped with a rotational stop (15).

18. Modular container according to claim 16, wherein said hinges are equipped with detent elements (14) which prevent excessive rotation of said cover on said hinges.

19. Modular container according to claim 1, wherein said front panel (17) of said upper section (1) depends from a front edge of the cover plate (16).

20. Modular container according to claim 1, wherein said front panels of said drawers and said upper section are equipped with means (31) for displaying contents lists.

* * * * *